(12) United States Patent
Valkoun et al.

(10) Patent No.: US 11,654,030 B2
(45) Date of Patent: May 23, 2023

(54) STANDALONE ANTERIOR LUMBER INTERBODY SPACER

(71) Applicant: Astura Medical Inc., Carlsbad, CA (US)

(72) Inventors: Anthony Valkoun, Carlsbad, CA (US); Thomas Purcell, Carlsbad, CA (US)

(73) Assignee: Astura Medical Inc., Irving, TX (US)

( * ) Notice: Subject to any disclaimer, the term of this patent is extended or adjusted under 35 U.S.C. 154(b) by 0 days.

(21) Appl. No.: 17/031,885

(22) Filed: Sep. 24, 2020

(65) Prior Publication Data
US 2021/0369466 A1 Dec. 2, 2021

Related U.S. Application Data

(60) Provisional application No. 62/905,384, filed on Sep. 24, 2019.

(51) Int. Cl.
*A61F 2/44* (2006.01)
*A61F 2/30* (2006.01)

(52) U.S. Cl.
CPC ............ *A61F 2/442* (2013.01); *A61F 2/4455* (2013.01); *A61F 2002/30505* (2013.01); *A61F 2002/30507* (2013.01)

(58) Field of Classification Search
CPC ...... A61F 2/4455; A61F 2/4465; A61F 2/447; A61B 17/7059; A61B 17/80; A61B 17/8033; A61B 17/8042
See application file for complete search history.

(56) References Cited

U.S. PATENT DOCUMENTS

| | | | | |
|---|---|---|---|---|
| 5,253,543 A * | 10/1993 | Carlson | ................... | B63H 25/10 403/328 |
| 5,458,642 A * | 10/1995 | Beer | ..................... | A61F 2/4425 606/247 |
| 6,454,806 B1 * | 9/2002 | Cohen | ................... | A61F 2/4455 623/17.15 |
| 8,667,875 B2 * | 3/2014 | Haman | ................... | B25B 21/02 81/463 |
| 2004/0153065 A1 * | 8/2004 | Lim | ....................... | A61F 2/4465 606/53 |
| 2005/0159813 A1 * | 7/2005 | Molz | ....................... | A61F 2/447 623/17.11 |
| 2005/0165400 A1 * | 7/2005 | Fernandez | ......... | A61B 17/8057 606/291 |
| 2007/0233253 A1 * | 10/2007 | Bray | ..................... | A61F 2/4455 623/17.11 |
| 2008/0281425 A1 * | 11/2008 | Thalgott | .................. | A61F 2/447 623/17.16 |
| 2009/0182430 A1 * | 7/2009 | Tyber | .................... | A61F 2/4465 606/301 |
| 2010/0057206 A1 * | 3/2010 | Duffield | .................... | A61F 2/44 606/279 |

(Continued)

OTHER PUBLICATIONS

International Search Report and Written Opinion in PCT Application No. PCT/US2020/052595 dated Sep. 24, 2020.

*Primary Examiner* — Jan Christopher L Merene
(74) *Attorney, Agent, or Firm* — Michael R. Shevlin (57) ABSTRACT

Disclosed is a standalone anterior lumbar interbody spacer that includes a lumbar spacer body and lumbar plate with a unique locking system to rigidly couple the spacer body and plate via a spring loaded lock tab.

14 Claims, 6 Drawing Sheets

(56) References Cited

U.S. PATENT DOCUMENTS

| | | | |
|---|---|---|---|
| 2010/0145455 A1* | 6/2010 | Simpson | A61F 2/44 623/17.16 |
| 2010/0305704 A1* | 12/2010 | Messerli | A61F 2/4455 623/17.16 |
| 2010/0312345 A1* | 12/2010 | Duffield | A61F 2/4455 623/17.16 |
| 2011/0130835 A1* | 6/2011 | Ashley | A61F 2/4455 623/17.11 |
| 2012/0016479 A1* | 1/2012 | Pisharodi | A61F 2/442 623/17.16 |
| 2013/0006357 A1* | 1/2013 | Krueger | A61F 2/44 623/17.13 |
| 2014/0039623 A1* | 2/2014 | Lott | A61F 2/30744 623/17.16 |
| 2014/0214166 A1* | 7/2014 | Theofilos | A61F 2/4455 623/17.16 |
| 2017/0333088 A1 | 11/2017 | Lee et al. | |
| 2017/0360487 A1 | 12/2017 | Moseley et al. | |
| 2018/0185163 A1 | 7/2018 | Weiman et al. | |
| 2020/0330239 A1* | 10/2020 | Davenport | A61F 2/4455 |
| 2021/0045892 A1* | 2/2021 | Rogers | A61F 2/4425 |

\* cited by examiner

SECTION A-A
FIG. 5

FIG. 6

SECTION B-B
FIG. 7

STANDALONE ANTERIOR LUMBER INTERBODY SPACER

CROSS-REFERENCE TO RELATED APPLICATIONS

This application claims the benefit of U.S. Provisional Application No. 62/905,384 filed Sep. 24, 2019, which is incorporated herein by reference.

FIELD

The present invention relates generally to the field of surgery, and more specifically, to an anterior lumbar interbody spacer for placement in intervertebral space between adjacent vertebrae during anterior lumbar spinal fixation.

BACKGROUND

A spinal disc can become damaged as a result of degeneration, dysfunction, disease and/or trauma. Conservative treatment can include non-operative treatment through exercise and/or pain relievers to deal with the pain. Operative treatment options include disc removal and replacement using an interbody spacers such as anterior cervical interbody fusion (ACIF), anterior lumbar interbody fusion (ALIF), direct lateral interbody fusion (DLIF) (also known as XLIF), posterior lumbar interbody fusion (PLIF), and transforaminal lumbar interbody fusion (TLIF).

The interbody spacers are placed in the interdiscal space between adjacent vertebrae of the spine, resulting in spinal fusion of the adjacent vertebra wherein two or more vertebrae are joined together (fused) by way of interbody spacers, sometimes with bone grafting, to form a single bone. The current standard of care for interbody fusion requires surgical removal of all or a portion of the intervertebral disc. After removal of the intervertebral disc, the interbody spacer is inserted in the space between the adjacent vertebrae.

Ideally, the interbody spacer should stabilize the intervertebral space and allow fusion of the adjacent vertebrae. Moreover, during the time it takes for fusion to occur, the interbody spacer body should have sufficient structural integrity to withstand the stress of maintaining the space without substantially degrading or deforming and have sufficient stability to remain securely in place prior to actual bone ingrowth fusion.

The interbody spacers are typically one piece that are assembled at the manufacturing stage. Many different sizes are made, which results in a large inventory of plate/spacer body combinations, as well as large sterilization/shipping caddies to facilitate transfer of spacers large interbody spacers. In addition, typical interbody spacers require a secondary element to install the plate in-situ to inhibit fixation screw migration. This secondary action is time consuming and cumbersome when the surgical procedure is time sensitive.

Some prior art designs utilized titanium arms for distraction, this places a large amount of force on the PEEK spacer body, potentially damaging the spacer during assembly. This increased distraction force requires a large assembly tool to overcome the titanium arms and makes disassembly difficult.

It would be desirable to provide an interbody spacer with modularity and functionality to decreased inventory size.

SUMMARY

Disclosed is a standalone anterior lumbar interbody spacer that includes a lumbar spacer body and lumbar plate with a unique locking system that rigidly couples the spacer body and plate via a spring loaded lock tab.

The locking system include locking features designed to engage with the spring loaded lock tab to lock the lumbar spacer body and lumbar plate together. The locking features are part of the lumbar plate protrusion having tab distraction geometry and lock geometry. The tab distraction geometry includes an inclined or ramped portion and the lock geometry includes a tab recess or pocket. The distraction geometry is such that as the spacer body and plate are coupled, the inclined or ramped portion will engage spring loaded lock tab and push the spring loaded lock tab in so that is can slide on the surface. Once the plate and spacer body are completely joined, the spring loaded lock tab reaches the tab recess or pocket, allowing the spring loaded lock tab to return to its original position within the recess or pocket, thereby locking the lumbar spacer body and lumbar plate. The tab engaging the recess may provide an audible click sound the let the user know that the parts are joined and locked together.

DETAILED DESCRIPTION

The invention is direct to an anterior lumbar interbody spacer that is a modular two piece design comprising a lumbar spacer body and plate that are designed to lock together via a lock tab. With this design, each of the components are provided in various sizes and configurations so that the surgeon can pick or choose the desired spacer body configuration and size. The surgeon can then select the desired plate configuration and join the two together. The lumbar spacer body and plate have engagement features that are configured to rigidly couple them together via the lock tab to form the anterior lumbar interbody spacer.

Figure 1A:
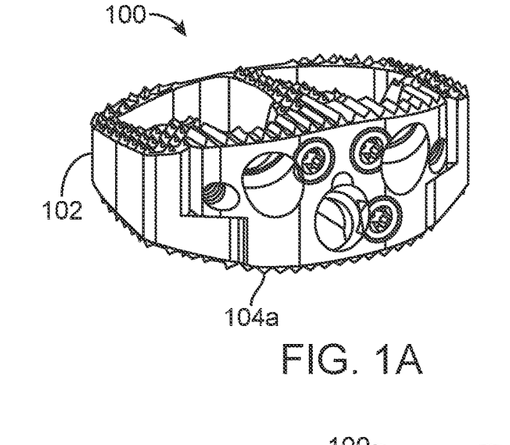
FIGS. 1A-1C show various configurations or variations of a modular lumbar interbody spacer having a lumbar spacer body coupled with different lumbar plates.
Figure 1B:
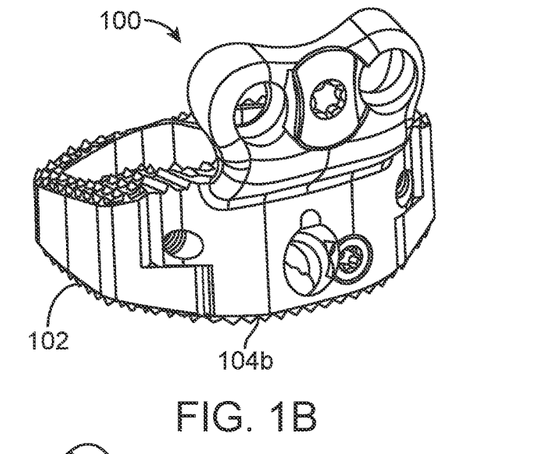
Figure 1C:
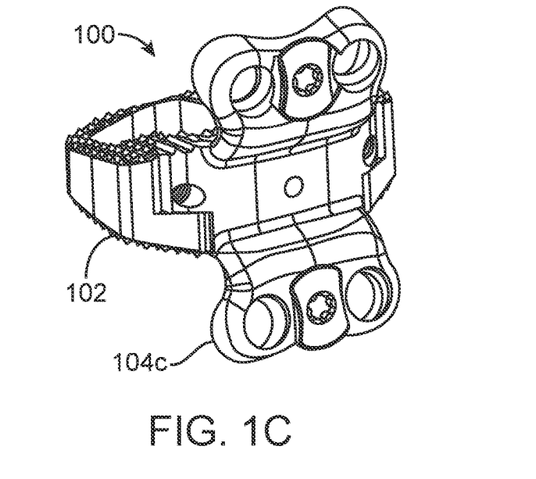

FIGS. 1A-1C show three configurations or variations of a modular anterior lumbar interbody spacer 100 comprising a lumbar spacer body 102 coupled with different lumbar plate 104 configurations or profile options. For example, FIG. 1A shows a Zero 104a, FIG. 1B shows a Half 104b, and FIG. 1C shows a Full 104c.

Figure 2A:
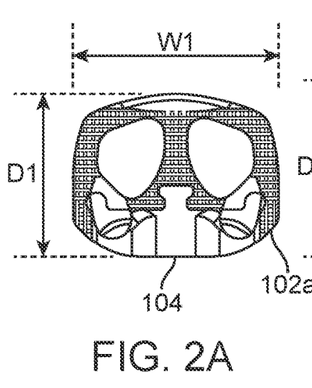
FIGS. 2A-2C show various configurations or variations of a lumbar interbody spacer with different lumbar spacer body footprints or configurations coupled with a lumbar plate.
Figure 2B:
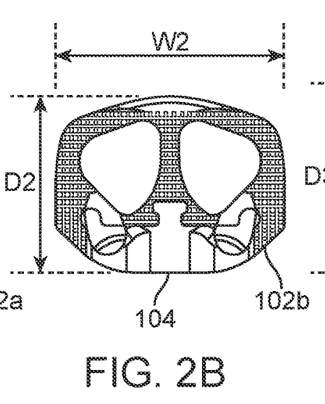
Figure 2C:
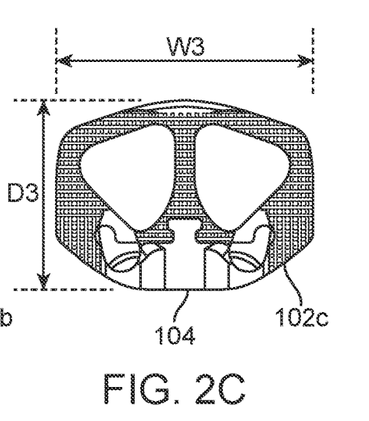

FIGS. 2A-2C show three configurations or variations of an anterior lumbar interbody spacer 100 comprising a three different lumbar spacer body footprints or configurations coupled with a lumbar plate 104. The lumbar spacer body configurations may include various footprints having different widths W, depths D, heights and sagittal profiles. For example, FIG. 2A shows a lumbar spacer body 102a with a 24×30 mm footprint, FIG. 2B shows a lumbar spacer body 102b with a 26×34 mm footprint, and FIG. 2C shows a lumbar spacer body 102c with a 28×38 mm footprint, the heights of the spacer bodies may include five heights from 10 mm-18 mm @2 mm increments, and three sagittal profiles, 7°, 12°, 30°.

Figure 3:
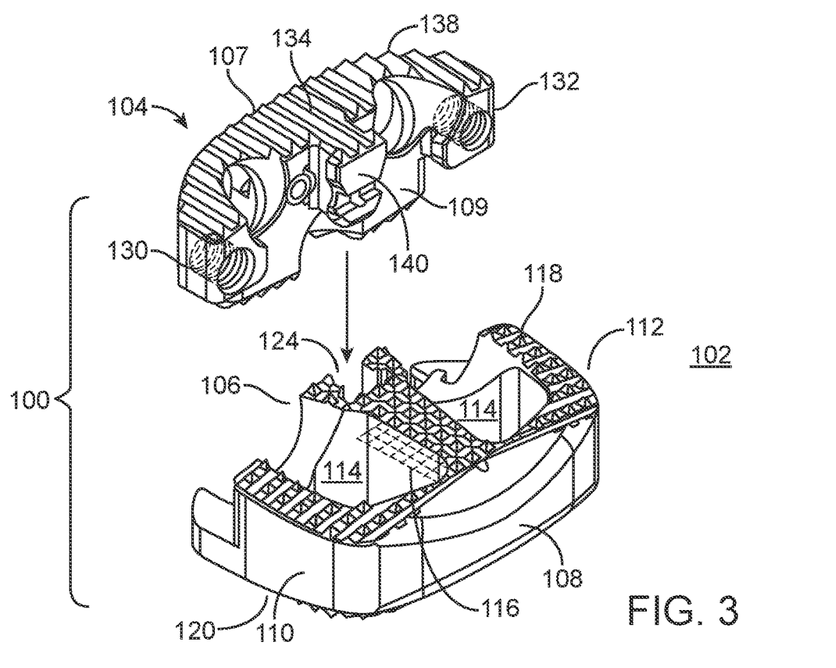
FIG. 3 shows an exploded perspective view showing one embodiment of an anterior lumbar interbody spacer

FIG. 3 is an exploded perspective view showing an anterior lumber interbody spacer 100 comprising a lumbar spacer body 102 and a lumbar plate 104 having coupling features to rigidly affixed the lumbar spacer body 102 to the lumbar plate 104.

The lumbar spacer body 102 is generally rectangular is shape with a proximal end 106 and a distal end 108 connected by lateral sides 110, 112 with one or more central openings 114. In the embodiments shown, the lumbar spacer body 102 further includes a central wall 116 between the proximal and distal ends 106, 108. The lumbar spacer body further includes an upper surface 118 and lower surface 120. The upper and lower surfaces 118, 120 may include teeth 122, such as Pyramidal Teeth. In some embodiments the surfaces may be roughened acid etch or blasted. The proximal end 106 of the lumbar spacer body 102 includes a slot 124. The slot 124 may be a vertical slot from the upper surface.

The lumbar plate 104 includes a proximal end 107, a distal end 109 and right and left sides 130, 132. The plate further includes an upper surface 134 and lower surface 136. The upper and lower surfaces 134, 136 may include teeth 138 as pyramidal teeth. In some embodiments the surfaces may be roughened acid etch or blasted. The distal end 107 includes a protrusion 140.

Figure 4:
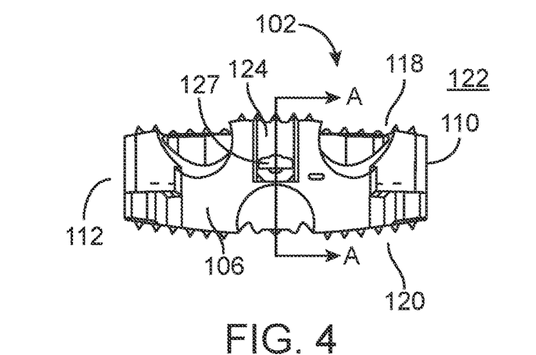
FIG. 4 shows a proximal view of the lumbar spacer body showing locking geometry
Figure 5:
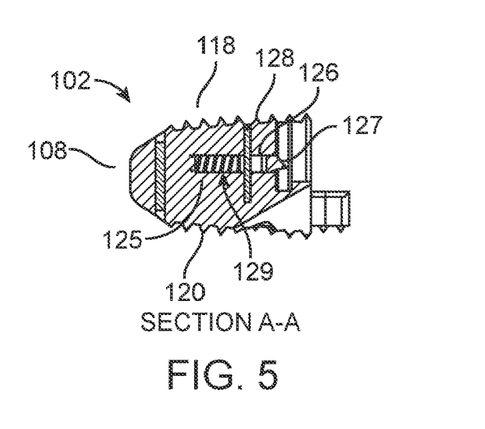
FIG. 5 shows a sectional view at A-A of the lumbar spacer body shown in FIG. 4.

FIG. 4 shows the proximal end 106 of the lumbar spacer body 102 and FIG. 5 is a cross-sectional view at A-A of the lumbar spacer body 102. The lumbar spacer body 102 having a spring loaded lock tab 126 configured to engage the protrusion 140 and coupled with a locking feature 154. The spring loaded lock tab 126 is coupled with a retaining pin 128 and a spring 129. The retaining pin 128 may be made of nitinol and the spring 129 may be elgiloy. The retaining pin 128 is positioned in a slotted portion of the spring loaded lock tab 126 to retain the spring loaded lock tab 126 and limit the inward and outward travel. The spring loaded lock tab 126, retaining pin 128 and spring 129 are slidable into a bore or hole 125 in the lumbar spacer body 102. The spring loaded lock tab 126 includes a ramped surface 127.

Figure 6:
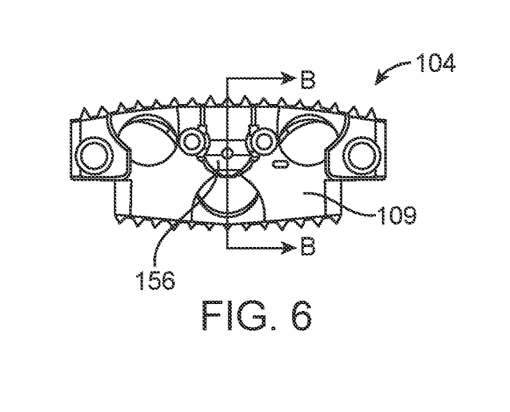
FIG. 6 shows a distal end of the lumbar plate.
Figure 7:
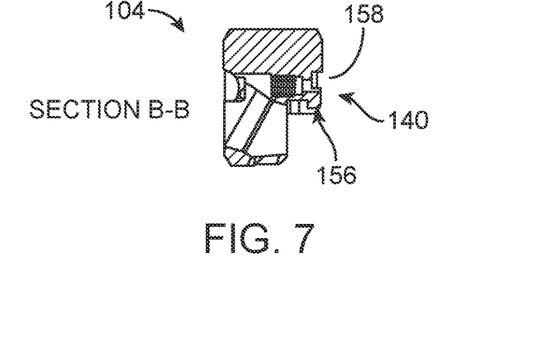
FIG. 7 shows a sectional view at B-B of the lumbar plate shown in FIG. 6.

FIG. 6 shows the distal end 125 of the lumbar plate 104 and FIG. 7 is a cross-sectional view of the lumbar plate 102. The protrusion 140 of the lumbar plate 104 may include distraction geometry 152 and lock geometry 154.

Figure 8:
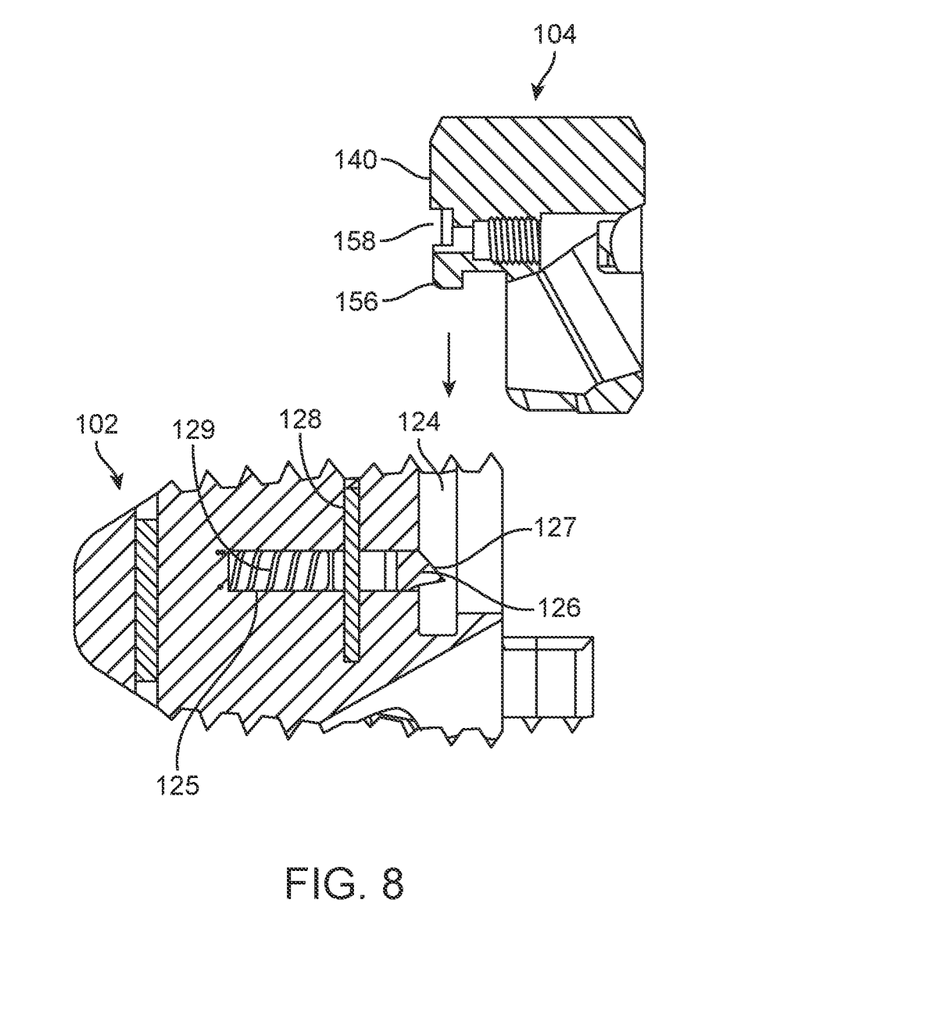
FIG. 8 shows the assembly of the lumbar plate into the lumbar spacer body.

FIG. 8 shows the assembly of the lumbar plate 104 into the lumbar spacer body 102. The protrusion 140 is inserted into the slot 124

The distraction geometry of the lumbar plate 104 includes a tab compression portion and a tab locking portion. The tab compression portion includes an inclined or ramped portion 156 and the tab locking portion includes a tab engagement recess or tab lock recess 158. As the protrusion 140 is slid into the slot 146, the inclined or ramped portion 156 engages the ramped surface 127 of the spring loaded lock tab 126 and forces the spring loaded lock tab 126 to slide inward against the spring 129. Once the lumbar plate 104 and lumbar spacer body 102 are completely joined, the spring loaded lock tab 126 reaches the lock geometry recess or pocket 158, allowing the spring loaded lock tab 126 to return to its original position, thereby locking the lumbar plate 104 to the lumbar spacer body 102. The movement of the spring loaded lock tab 126 into the geometry recess or pocket 158 may provide an audible click sound the let the user know that the parts are joined and locked together.

Figure 9:
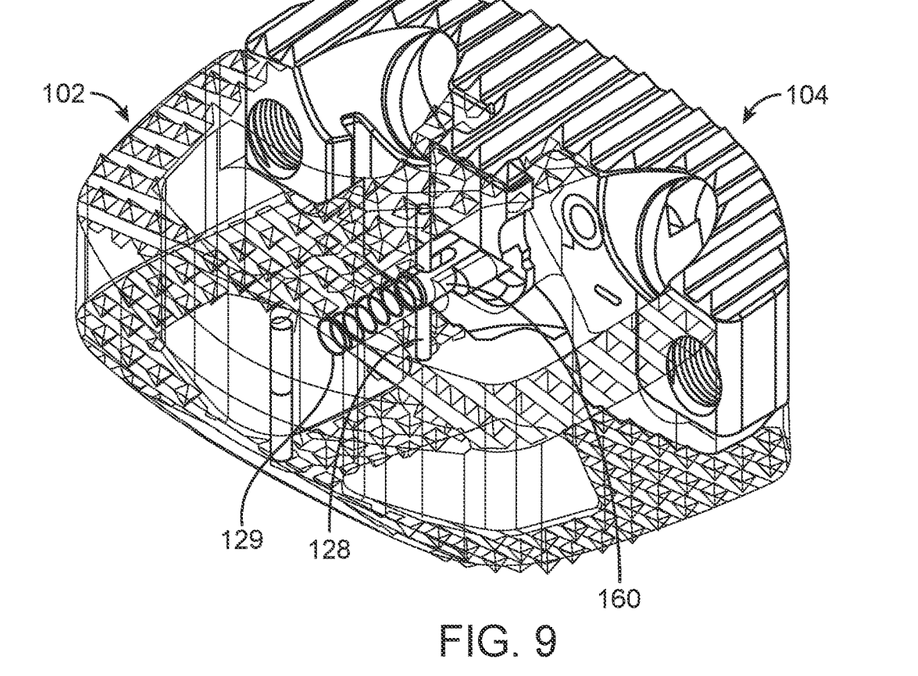
FIG. 9 shows a perspective view of the anterior lumbar interbody spacer.
Figure 10:
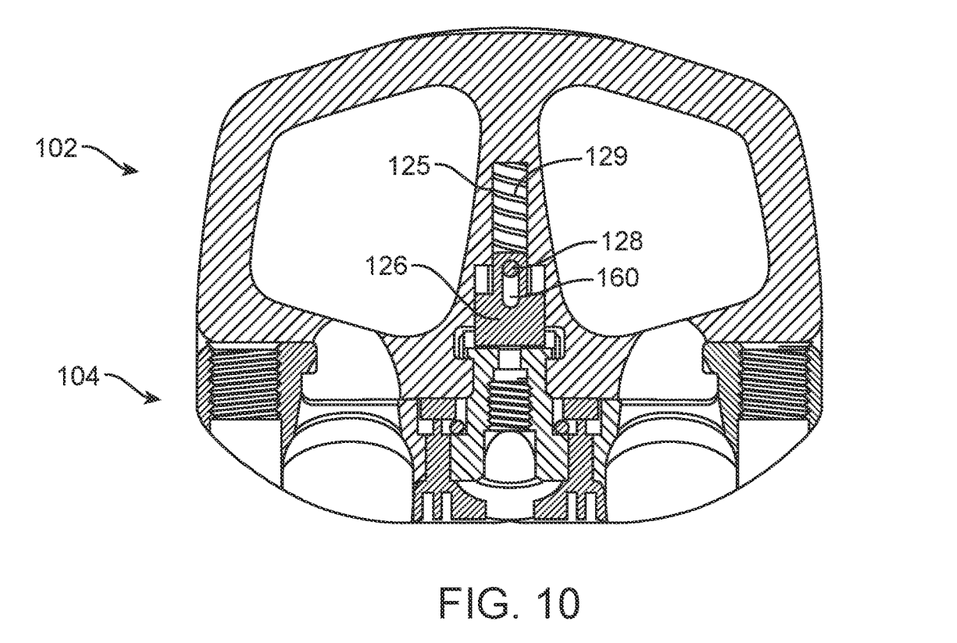
FIG. 10 shows a sectional view of the anterior lumbar interbody spacer at C-C of FIG. 9.

FIG. 9 is a perspective view of the anterior lumbar interbody spacer 100 and FIG. 10 is a sectional view showing the lumbar plate 104 coupled with the lumbar spacer body 102. The lumbar spacer body 102 is shown as transparent to show features of the spring loaded lock tab 126. The spring loaded lock tab 126 includes a slot 160 sized for the retaining pin 128. The slot 160 retains the spring loaded lock tab 126 in the bore 125 and limits the inward and outward movement. The spring loaded lock tab 126 is also coupled to the spring 129. The spring 129 supplies a force to the spring loaded lock tab 126 so that the spring loaded lock tab 126 is naturally in the outward position. When the spring loaded lock tab 126 engages the protrusion 140, the spring loaded lock tab 126 compresses the spring 129. Once the spring loaded lock tab 126 reaches the pocket 158, the spring forces the spring loaded lock tab 126 to the outward position within the pocket 158, locking the lumbar plate 104 with the lumbar spacer body 102.

In some embodiments, the anterior lumbar interbody spacer 100 will utilize PEEK or titanium (TI) lumbar spacer body 102 in conjunction with a titanium (TI) lumbar plate 104.

Lumbar plate 104a includes three fastener holes 150, two fastener holes are tilted at an upward angle so that the engagement fastener engages the vertebra above the anterior lumbar interbody spacer 100 and the other fastener hole is tilted at a downward angle so that the bone engagement fastener engages the vertebra below the anterior lumbar interbody spacer 100. Lumbar plate 104b includes three fastener holes, a center fastener hole tilted at a downward angle so that the bone engagement fastener engages the vertebra below the lumbar spacer body 102 and two outer holes are tilted at an upward angle so that the engagement fasteners engage the vertebra above the lumbar spacer body 102. Lumbar plate 104c includes four fastener holes, an upper pair of fastener holes tilted at an upward angle so that the engagement fasteners engage the vertebra above the lumbar spacer body 102 and a lower pair of fastener holes tilted at a downward angle so that the bone engagement fasteners engage the vertebra below the lumbar spacer body 102.

Figure 11:
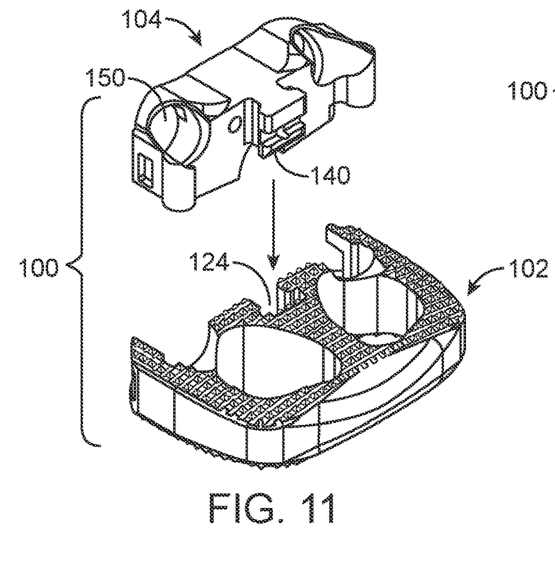
FIG. 11 shows assembly of the anterior lumbar interbody spacer.

FIG. 11 shows assembly of the anterior lumbar interbody spacer 100 that may be assembled on the back table in the operating room (OR). The anterior lumbar interbody spacer 100 can be assembled from a variety of lumbar plates 104, such as 140a, 104b or 104c, and lumbar spacer body 102, such as 102a, 102b, 102c To assemble the anterior lumbar interbody spacer 100, the protrusion 140 of the lumbar plate 104 is slid into the slot 124 of the lumbar spacer body 102 in a vertical direction. The geometry of the protrusion 140 is such that it will force the spring loaded lock tab 126 to distract into a bore 125 in the spacer body. Once the lumbar plate 104 has been sufficiently inserted into the lumbar spacer body 102, the lock geometry 154 on the lumbar plate 104 will allow for the spring loaded tab 126 to return to its original position in pocket 158, thereby locking the lumbar plate 104 with the lumbar spacer body 102. Engaging the recess 158 may provide an audible click sound the let the user know that the parts are joined and locked together.

Figure 12:
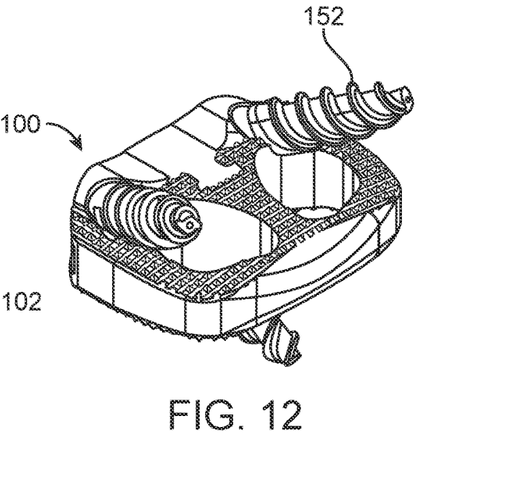
FIG. 12 shows the anterior lumbar interbody spacer 100 in the implanted configuration.

FIG. 12 shows the anterior lumbar interbody spacer 100 in the implanted configuration. The lumbar plate 104 includes two more fastener holes 150 sized to receive bone engagement fasteners 152 configured to anchor the anterior lumbar interbody spacer 100 between two vertebrae of the spine.

Figure 13A:
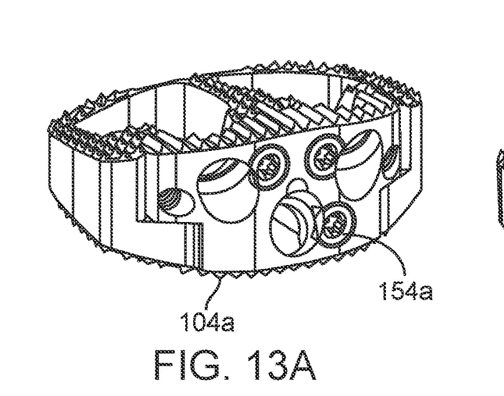
FIGS. 13A-13C show different embodiments of bone screw locking features.
Figure 13B:
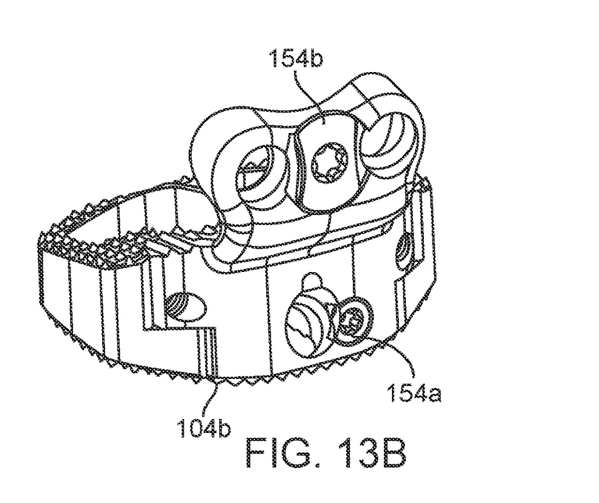
Figure 13C:
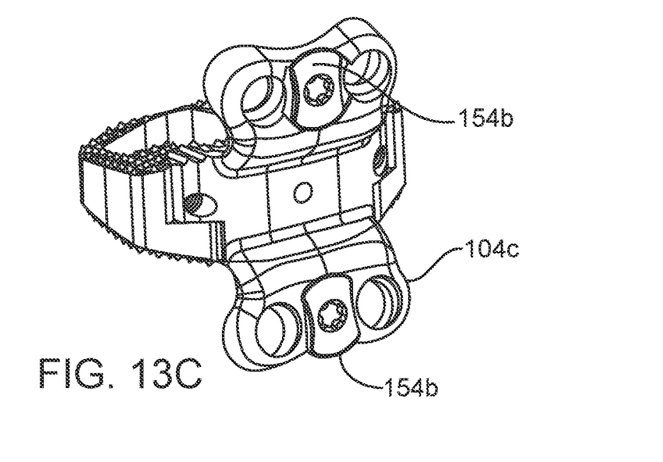

FIGS. 13A-13C show different embodiments of bone screw locking features, such as a single hole locking feature 154 or a double hole locking feature 156, covering a portion of the hole 150. to prevent the bone fasteners 152 from withdrawing from the fastener holes 150. FIG. 13A shows lumbar plate 104a having three fastener holes 150 and three locking features 154 positioned near the fastener holes 150 with a portion of the locking feature, such as a head portion, covering part of the fastener holes 150. FIG. 13B shows lumbar plate 104b having three fastener holes 150 and both the single hole locking feature 154 and double hole locking feature 156 three locking features shows use of both single hole locking feature 154 and double hole locking feature 156. FIG. 13C shows lumbar plate 104c having four fastener holes 150 and two double hole locking feature 156c.

The present invention requires relatively small amounts of assembly force due to the elasticity of the spring loaded tab and spring, in addition, the tab can be easily distracted utilizing a secondary instrument, allowing for simple and fast implant disassembly.

Figure 14:
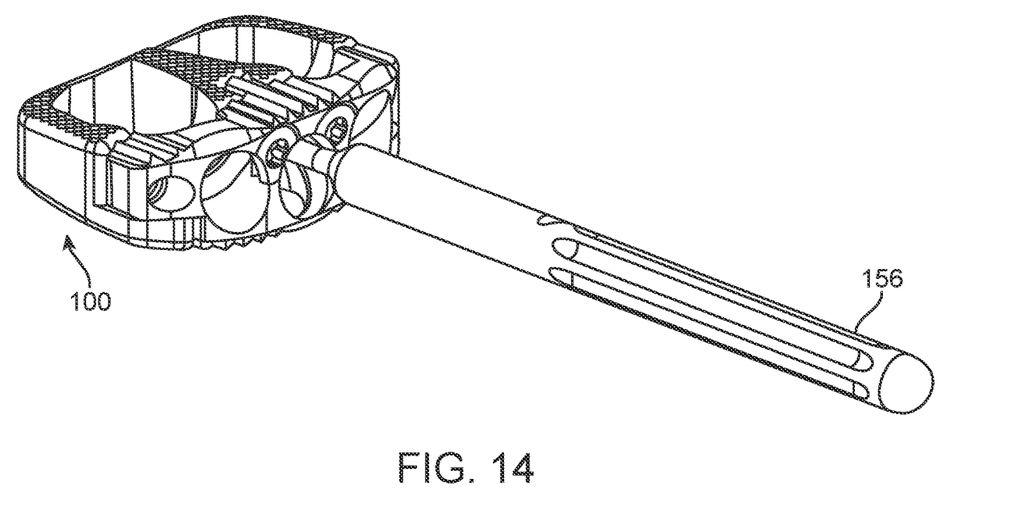
FIG. 14 shows an implant disassembly tool.
Figure 15:
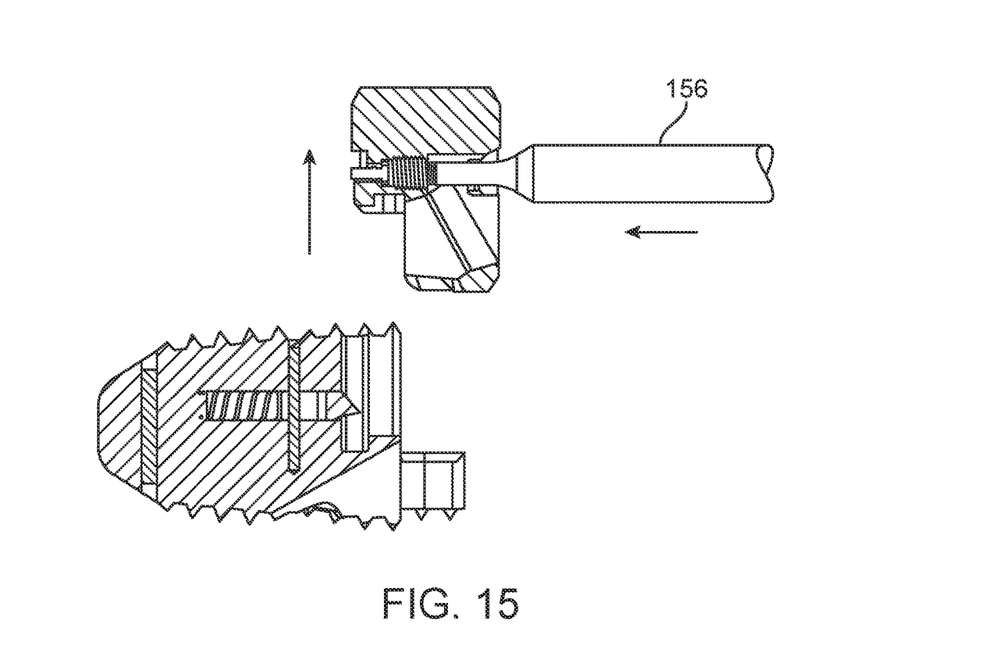
FIG. 15 shows a sectional view of the implant disassembly tool disengaging the spring loaded lock tab.

FIG. 14 shows an implant disassembly tool 156 that is used to disengage the spring loaded lock tab 126 for implant disassembly shown in FIG. 15. The implant disassembly tool 156 is inserted through a hole in the lumbar plate and pushes the spring loaded lock tab 126 to disengage the lumbar plate 104 from the lumbar spacer body 102, pushing the spring loaded lock tab 126 into.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. A modular interbody spacer for placement between adjacent vertebrae comprising:
    a spacer body selected from a group of interchangeable spacer bodies having upper and lower vertebrae engagement surfaces and a proximal end having a vertical slot from the upper surface with a bore or hole;
    a spring loaded lock tab and a spring slidable within the bore or hole; and
    a fixation plate selected from a group of interchangeable fixation plates having upper and lower bone vertebrae surfaces and a distal end coupled to the proximal end of the spacer body, the fixation plate incudes:
        one or more fastener holes on a proximal end sized to receive a bone engagement fastener to attach the fixation plate to:
            the vertebra above or below the spacer body, or
            both the vertebra above and below the spacer body; and
        a protrusion on the distal end configured to slidably insert in the vertical slot in a vertical direction,
            a first portion of the protrusion is configured to compress the spring loaded lock tab during insertion, and
            a second portion of the protrusion is configured to lock the spring loaded lock tab when the fixation plate and spacer body are completely joined.

2. The interbody spacer of claim 1, wherein the first portion of the protrusion includes an inclined or ramped portion configured to engage and move the spring loaded lock tab and spring inward in the bore or hole.

3. The interbody spacer of claim 1, wherein the second portion of the protrusion includes a tab engagement recess configured to engage and allow the spring loaded lock tab and spring to move outward from the bore and lock the spring loaded lock tab.

4. The interbody spacer of claim 1, wherein the spring loaded lock tab includes a slotted portion and a retaining pin positioned in the slotted portion to retain the spring loaded lock tab and limit the inward and outward travel.

5. The interbody spacer of claim 1, where the proximal end of the fixation plate includes a hole configured to receive a disassembly tool to disengage the spring loaded lock tab.

6. A modular interbody spacer for placement between adjacent vertebrae comprising:
    a spacer body selected from a group of interchangeable spacer bodies having upper and lower vertebrae engagement surfaces and a proximal end having a vertical slot from the upper surface with a bore or hole;
    a spring loaded lock tab and a spring slidable within the bore or hole; and
    a fixation plate selected from a group of interchangeable fixation plates having upper and lower bone vertebrae surfaces and a distal end coupled to the proximal end of the spacer body, the fixation plate incudes:
        one or more fastener holes on a proximal end sized to receive a bone engagement fastener to attach the fixation plate to:
            the vertebra above or below the spacer body, or
            both the vertebra above and below the spacer body; and
        a protrusion the distal end configured to slidably insert in the vertical slot in a vertical direction,
            a first portion of the protrusion includes an inclined or ramped portion configured to compress the spring loaded lock tab during insertion, and
            a second portion of the protrusion includes a tab engagement recess configured to lock the spring loaded lock tab when the fixation plate and spacer body are completely joined.

7. The interbody spacer of claim 6, wherein the inclined or ramped portion is configured to engage and move the spring loaded lock tab and spring inward in the bore or hole.

8. The interbody spacer of claim 6, wherein the tab engagement recess is configured to allow the spring loaded lock tab and spring to move outward from the bore and lock the spring loaded lock tab.

9. The interbody spacer of claim 6, wherein the spring loaded lock tab includes a slotted portion and a retaining pin positioned in the slotted portion to retain the spring loaded lock tab and limit the inward and outward travel.

10. The interbody spacer of claim 6, where the proximal end of the fixation plate includes a hole configured to receive a disassembly tool to disengage the spring loaded lock tab.

11. A modular interbody spacer for placement between adjacent vertebrae comprising:
- a spacer body selected from a group of interchangeable spacer bodies having upper and lower vertebrae engagement surfaces and a proximal end having a vertical slot from the upper surface with a bore or hole;
- a spring loaded lock tab and a spring slidable within the slot, bore or hole; and
- a fixation plate selected from a group of interchangeable fixation plates having upper and lower vertebrae engagement surfaces and a distal end coupled to the proximal end of the spacer body, the fixation plate incudes:
  - one or more fastener holes on a proximal end sized to receive a bone engagement fastener to attach the fixation plate to:
    - the vertebra above or below the spacer body, or
    - both the vertebra above and below the spacer body; and
  - a protrusion on the distal end configured to slidably insert in the vertical slot in a vertical direction,
    - a first portion of the protrusion includes an inclined or ramped portion configured to engage and move the spring loaded lock tab and spring inward in the bore or hole, and
    - a second portion of the protrusion includes a tab engagement recess configured to allow the spring loaded lock tab and spring to move outward from the bore and lock the spring loaded lock tab when the fixation plate and spacer body are completely joined.

12. The interbody spacer of claim 11, wherein the spring loaded lock tab includes a slotted portion and a retaining pin positioned in the slotted portion to retain the spring loaded lock tab and limit the inward and outward travel.

13. The interbody spacer of claim 11, wherein the proximal end of the fixation plate includes a hole configured to receive a disassembly tool to disengage the spring loaded lock tab.

14. The interbody spacer of claim 11, wherein the proximal end of the fixation plate includes bone screw locking features.

* * * * *